(12) United States Patent
Barfurth et al.

(10) Patent No.: US 7,939,616 B2
(45) Date of Patent: May 10, 2011

(54) ORGANOFUNCTIONAL SILOXANE MIXTURES

(75) Inventors: Dieter Barfurth, Rheinfelden (DE); Helmut Mack, Traunstein (DE)

(73) Assignee: Evonik Degussa GmbH, Essen (DE)

( * ) Notice: Subject to any disclaimer, the term of this patent is extended or adjusted under 35 U.S.C. 154(b) by 1197 days.

(21) Appl. No.: 10/555,984

(22) PCT Filed: Mar. 18, 2004

(86) PCT No.: PCT/EP2004/050326
§ 371 (c)(1),
(2), (4) Date: Sep. 26, 2006

(87) PCT Pub. No.: WO2004/101652
PCT Pub. Date: Nov. 25, 2004

(65) Prior Publication Data
US 2007/0032622 A1    Feb. 8, 2007

(30) Foreign Application Priority Data

May 13, 2003   (DE) .................... 103 21 320

(51) Int. Cl.
    *C08G 77/22*    (2006.01)
(52) U.S. Cl. ............ 528/30; 525/479; 528/38; 528/415; 528/425
(58) Field of Classification Search .......... 528/86, 528/415, 425
    See application file for complete search history.

(56) References Cited

U.S. PATENT DOCUMENTS

| | | | |
|---|---|---|---|
| 4,172,189 A | 10/1979 | Muller et al. | |
| 4,413,104 A * | 11/1983 | Deubzer et al. ............... | 525/479 |
| 5,079,312 A * | 1/1992 | Isozaki et al. ................. | 525/479 |
| 6,133,466 A | 10/2000 | Edelmann et al. | |
| 6,239,194 B1 | 5/2001 | Standke et al. | |
| 6,251,989 B1 | 6/2001 | Edelmann et al. | |
| 6,255,513 B1 | 7/2001 | Standke et al. | |
| 6,361,871 B1 | 3/2002 | Jenkner et al. | |
| 6,395,858 B1 * | 5/2002 | Mack et al. ..................... | 528/38 |
| 6,403,228 B1 | 6/2002 | Mack et al. | |
| 6,444,315 B1 | 9/2002 | Barfurth et al. | |
| 6,500,883 B1 | 12/2002 | Mack et al. | |
| 6,528,585 B1 | 3/2003 | Standke et al. | |
| 6,534,667 B1 | 3/2003 | Standke et al. | |
| 6,770,327 B2 | 8/2004 | Edelmann et al. | |
| 6,780,955 B2 | 8/2004 | Barfurth et al. | |
| 6,784,272 B2 | 8/2004 | Mack et al. | |
| 6,841,197 B2 | 1/2005 | Standke et al. | |
| 2002/0127415 A1 | 9/2002 | Standke et al. | |
| 2003/0134969 A1 | 7/2003 | Schlosser et al. | |
| 2004/0054048 A1 | 3/2004 | Barfurth et al. | |
| 2004/0192873 A1 * | 9/2004 | Okuhira et al. ................. | 528/25 |

FOREIGN PATENT DOCUMENTS

| | | |
|---|---|---|
| EP | 0 101 787 | 3/1984 |
| EP | 0 518 057 | 12/1992 |
| EP | 0 675 128 | 10/1995 |
| EP | 0 716 127 | 6/1996 |
| EP | 0 716 128 | 6/1996 |
| EP | 0 814 110 | 12/1997 |
| EP | 0 927 735 | 7/1999 |
| EP | 0 960 921 | 12/1999 |
| EP | 0 978 525 | 2/2000 |
| EP | 1 031 593 | 8/2000 |
| WO | WO 2004/101652 A1 | 11/2004 |

OTHER PUBLICATIONS

Andrianov, K. A. et al, "Methods of Synthesizing 1, n-Diethoxymethylchloromethylsiloxanes and Substitutions of the Chlorine in the Alpha-Chloromethyl Group", Journal of General Chemistry of the USSR, vol. 30, No. 7, pp. 2374-2377, Jul. 1960.

Vdovin, V. M. et al, "Addition of Alkoxysilanehydrides to Unsaturated Nitriles and Hydrogenation of the Omega-Cyanoalkylalkoxysilanes Obtained", Bulletin of the Academy of Sciences of the USSR, No. 11, pp. 1872-1876, Nov. 1961.

Wacker Silicones Brochure, "Einen Schritt Voraus Organofunktionelle Silane Von Wacker", Intelligent Industry Solutions (with English translation of pp. 8-11). [Retrieved on Jan. 5, 2011] [Retrieved from Internet<URL: http://www.wacker.com/cms/media/publications/downloads/6085_DE.pdf.

* cited by examiner

*Primary Examiner* — Randy Gulakowski
*Assistant Examiner* — Lindsay Nelson
(74) *Attorney, Agent, or Firm* — Oblon, Spivak, McClelland, Maier & Neustadt, L.L.P.

(57) ABSTRACT

The present Invention relates to a mixture comprising catenary, branched and for cyclic siloxanes of the general formula (I) where x is 1, 2 or 3, the substituents R are (i) organofunctional groups selected from —$CH_2$—SH, —$CH_2$—S—(CO)—R', —$CH_2$—(O—$C_2H_4$)$_a$—OH with a=1 to 10, —$CH_2$(O—$C_2H_4$)$_b$—OR' with b=1 to 40, —($CH_2$)—$NH_2$, —($CH_2$)—NHR', —($CH_2$)—NR'$_2$, —($CH_2$)—NH($CH_2$)$_2$—$NH_2$, —($CH_2$)—N[($CH_2$)$_2$—$NH_2$]$_2$ and —($CH_2$)—NH($CH_2$)$_2$—NH($CH_2$)$_2$—$NH_2$, In which R' is a linear, branched or cyclic alkyl group having 1 to 18 carbon atoms or an aryl group having 6 to 12 carbon atoms, (ii) hydroxyl, methoxy, ethoxy, 2-methoxyethoxy, isopropoxy, n-propoxy, isobutoxy and for n-butoxy groupe, and (iii) where appropriate, alkyl, alkenyl, isoalkyl, cycloalkyl or fluorcalkyl groups having 1 to 18 carbon atoms or aryl groups having 6 to 12 carbon atoms, whit the proviso that not more than one organofunctional group (i) is attached per silicon atom, the quotient of the molar ratio of the moiety (ii) to silicon le from I to 2, and the degree of oligornerization for compounds of the general formula I is in the range from 2 to 50. The present invention also relates to a specific process for preparing said siloxane mixtures and also to their use.

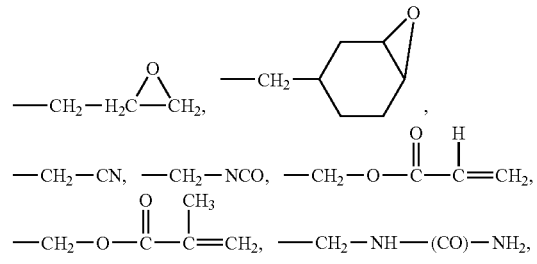

19 Claims, No Drawings

ORGANOFUNCTIONAL SILOXANE MIXTURES

The present invention relates to silane mixtures comprising novel organofunctional siloxanes.

The present invention further relates to a process for preparing said mixtures and to their use.

1-Organomethylchlorosilanes and 1-organomethylalkoxysilanes have long been known. 1-Aminomethylsilanes, for example, are obtainable by reacting a chloromethylsilane with ammonia or an organic amine. Thus one possible reaction is that of a chloromethylalkoxysilane with ammonia or ethylenediamine to give (following removal of the salt load produced) a 1-aminomethylalkoxysilane or N-(2-aminoethyl)-1-aminomethylalkoxysilane, respectively.

Furthermore, organosiloxanes or mixtures thereof are obtained, for example, by targeted hydrolysis or condensation of organofunctional chlorosilanes or alkoxysilanes. A particular problem associated with the preparation of polyfunctional siloxane oligomers are the sharply different hydrolysis or condensation characteristics of the individual organoalkoxysilanes and organochlorosilanes.

EP 0 716 128 A2, EP 0 716 127 A2, and EP 0 675 128 A1 disclose aqueous solutions of 3-aminopropyl-functional and OH-functional organosilanes and organosiloxanes. In these organosilane systems hydrolysis is virtually complete.

EP 0 518 057 A1 and DE 196 24 032 A1 disclose mixtures of catenary and cyclic vinyl-functional and alkyl-functional siloxane oligomers which also carry alkoxy groups. Such mixtures are used for example, to make mineral surfaces and pulverulent materials repellent to water, as crosslinking agents for thermoplastic polyolefins, and as adhesion promoters in adhesives and sealants.

Moreover, DE 198 34 990 discloses mixtures of catenary and cyclic siloxane oligomers containing 3-acryloyloxypropyl or 3-methacryloyloxypropyl groups.

Siloxane oligomers of this kind can be used for surface treatment or modification of mineral or pulverulent substances, such as titanium dioxide, talc, clay, silicas, quartz, kaolin, aluminum hydroxide, magnesium hydroxide, bentonite, montmorillonite, mica (muscovite mica), calcium carbonate (chalk, dolomite), for example. Said siloxane oligomers are also used as adhesion promoters in, for example, kaolin-filled rubber compounds, in adhesives and sealants, in inks and paints, and in the construction industry.

It was an object of the present invention to provide further mixtures comprising organofunctional siloxanes.

This object is achieved in accordance with the invention as specified in the claims.

Surprisingly it has been found that a mixture of catenary, branched, and cyclic siloxanes of the general formula $$R_xSiO_{(4-x)/2} \quad (I)$$

is obtainable
where, in formula I,
x is 1, 2 or 3,
the substituents R are
(I) organofunctional groups selected from —$CH_2$—SH, —$CH_2$S—(CO)—R', —$CH_2$—$H_2C$—$CH_2$ (epoxy group), —$CH_2$—(cyclohexyl epoxy group),

—$CH_2$—CN, —$CH_2$—NCO, —$CH_2$—O—C(=O)—C(H)=$CH_2$,

—$CH_2$—O—C(=O)—C($CH_3$)=$CH_2$, —$CH_2$—NH—(CO)—$NH_2$,

—$CH_2$—(O—$C_2H_4$)$_a$—OH with a=1 to 10, —$CH_2$—(O—$C_2H_4$)$_b$—OR' with b=1 to 40, preferably with b=1 to 20, —($CH_2$)—$NH_2$, —($CH_2$)—NHR', —($CH_2$)—NR'$_2$, —($CH_2$)—NH($CH_2$)$_2$—$NH_2$, —($CH_2$)—N[($CH_2$)$_2$—$NH_2$]$_2$ and —($CH_2$)—NH($CH_2$)$_2$—NH($CH_2$)$_2$—$NH_2$, in which R' is a linear, branched or cyclic alkyl group having 1 to 18 carbon atoms or an aryl group having 6 to 12 carbon atoms, (ii) hydroxyl, methoxy, ethoxy, 2-methoxyethoxy, isopropoxy, n-propoxy, isobutoxy and/or n-butoxy groups, and (iii) where appropriate, alkyl, alkenyl, isoalkyl, cycloalkyl or fluoroalkyl groups having 1 to 18 carbon atoms or aryl groups having 6 to 12 carbon atoms, with the proviso that not more than one organofunctional group (i) is attached per silicon atom, the quotient of the molar ratio of the moiety (ii) to silicon is from 1 to 2, preferably from 1.2 to 1.6, and the degree of oligomerization for compounds of the general formula I is in the range from 2 to 50, preferably from 2 to 30, by using as component A at least one 1-organofunctional trialkoxysilane or one 1-organofunctional methylalkoxysilane and, where appropriate, as component B at least one alkyl-, alkenyl-, isoalkyl-, cycloalkyl- or fluoroalkyl-trialkoxysilane having 1 to 18 carbon atoms and/or phenyltrialkoxysilane and/or alkyl-, alkenyl-, isoalkyl-, cycloalkyl- or fluoroalkyl-methylalkoxysilane having 1 to 18 carbon atoms and/or phenylmethyldialkoxysilane and, where appropriate, as component C a tetraalkoxysilane, subjecting components A, where appropriate, B, and, where appropriate, C, in succession or in a mixture, to targeted hydrolysis and/or condensation using from 0.5 to 1.8 mol of water, preferably from 0.8 to 1.2 mol, per mole of Si and using from 0.1 to 10 times, preferably from 0.5 to 5 times, the amount by weight of methanol and/or ethanol and/or at least one alcohol corresponding to the alkoxy groups of (ii), based on the alkoxysilanes used, at a temperature of from 10 to 120° C., preferably from 25 to 90° C., more preferably from 35 to 80° C., and subsequently working up the product mixture by distillation under atmospheric pressure or under reduced pressure and at a liquid phase temperature of up to 120° C. During the workup of the crude product it is possible where appropriate to add an organic or inorganic acid in order to stabilize the system. Working up is appropriately accompanied by the removal from the product of the free alcohol and of any residues of the monomeric starting materials which have not undergone hydrolysis. Accordingly it is possible to provide a 1-organofunctional siloxane mixture which as compared with comparable prior art systems has an even lower organic constituent content, in particular a hydrolysis alcohol of high volatility and low flash point, which is therefore particularly advantageous in the light of the VOC problem. It is surprising, and hence likewise of particular advantage, that here as well the hydrolysis and/or condensation can be conducted targetedly without any additive extraneous to the system, such as a hydrolysis and/or condensation catalyst.

Siloxane mixtures of the invention that are obtained in this way are generally homogeneous, clear to slightly opalescent, colorless to weakly yellow-colored, storage-stable liquids of low viscosity which possess preferably a flash point >100° C. in order to improve the product safety.

By means of the mode of preparation set out above it is possible with advantage to produce siloxane mixtures of the invention which possess preferably a statistical distribution of differently functional, i.e., polyfunctional [—Si(R)(R)O—] units in the sense of claim 1.

Present systems are further distinguished from comparable systems by more effective wetting on surfaces.

It is also advantageous that the boiling point of the mixtures of the invention is generally situated at a temperature >200° C.

Systems of the invention can be applied advantageously both in concentrated form and in the form of an alcoholic or aqueous formulation or of a formulation comprising water and alcohol.

The present invention accordingly provides a mixture comprising catenary, branched and/or cyclic siloxanes of the general formula I $$R_xSiO_{(4-x)/2} \qquad (I)$$

where
x is 1, 2 or 3,
the substituents R are
(I) organofunctional groups selected from —CH$_2$—SH, —CH$_2$S—(CO)—R',

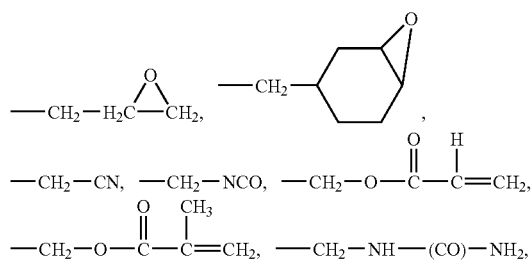

—CH$_2$—(O—C$_2$H$_4$)$_a$—OH with a=1 to 10, —CH$_2$—(O—C$_2$H$_4$)$_b$—OR' with b=1 to 40, —(CH$_2$)—NH$_2$, —(CH$_2$)—NHR', —(CH$_2$)—NR'$_2$, —(CH$_2$)—NH(CH$_2$)$_2$—NH$_2$, —(CH$_2$)—N[(CH$_2$)$_2$—NH$_2$]$_2$ and —(CH$_2$)—NH (CH$_2$)$_2$—NH(CH$_2$)$_2$—NH$_2$, in which R' is a linear, branched or cyclic alkyl group having 1 to 18 carbon atoms or an aryl group having 6 to 12 carbon atoms,
(ii) hydroxyl, methoxy, ethoxy, 2-methoxyethoxy, isopropoxy, n-propoxy, isobutoxy and/or n-butoxy groups, and
(iii) where appropriate, alkyl, alkenyl, isoalkyl, cycloalkyl or fluoroalkyl groups having 1 to 18 carbon atoms or aryl groups having 6 to 12 carbon atoms,
with the proviso that not more than one organofunctional group (i) is attached per silicon atom, the quotient of the molar ratio of the moiety (ii) to silicon is from 1 to 2, and the degree of oligomerization for compounds of the general formula I is in the range from 2 to 50.

Present siloxane mixtures preferably have an alkoxy group content of more than 0.001% by weight and less than 60% by weight, more preferably from 0.1 to 50% by weight, and with particular preference from 0.5 to 40% by weight, based on the weight of the siloxanes present.

In an inventive mixture the substituents R consist preferably of (i) 1-aminomethyl, N-(2-aminoethyl)-1-aminomethyl, N,N-di(2-aminoethyl)-1-aminomethyl, N—[N'-(2-aminoethyl)-2-aminoethyl)]-1-aminomethyl, N-methyl-1-aminomethyl, N-(n-butyl)-1-aminomethyl, N-cyclohexyl-1-aminomethyl, ureidomethyl or N-phenyl-1-aminomethyl groups and (ii) methoxy, ethoxy, 2-methoxyethoxy, propoxy and/or butoxy groups, and (iii), where appropriate, methyl, vinyl, ethyl, propyl, isobutyl, octyl, hexadecyl or phenyl groups.

The following are examples that may be given of some preferred systems of catenary and cyclic siloxane oligomers: 1-aminomethyl-/tridecafluorotetrahydro-1,1,2,2-tetrahydrooctyl-/hydroxy-, methoxy- or ethoxy-siloxane, the alkoxy groups being preferably methoxy or ethoxy groups, although ethoxy and methoxy groups can also be present alongside one another, and also hydroxyl groups.

The invention further provides a process for preparing an inventive mixture of catenary and cyclic siloxane oligomers by targeted hydrolysis and cocondensation using as component A at least one 1-organomethyl-functional trialkoxysilane or one 1-organomethyl-functional methyldialkoxysilane and, if desired, as component B, at least one alkyl-, alkenyl-, isoalkyl-, cycloalkyl- and/or fluoroalkyl-trialkoxysilane having 1 to 18 carbon atoms and/or phenyltrialkoxysilane and/or alkyl-, alkenyl-, isoalkyl-, cycloalkyl- and/or fluoroalkyl-methyldialkoxysilane having 1 to 18 carbon atoms and/or phenylmethyldialkoxysilane, and, where appropriate, as component C, a tetraalkoxysilane, subjecting the components A, where appropriate, B, and, where appropriate, C, in succession or in a mixture, to targeted hydrolysis and condensation using from 0.5 to 1.8 mol of water per mole of Si and from 0.1 to 10 times the amount by weight of at least one alcohol corresponding to the alkoxy groups of (ii), based on the alkoxysilanes used, at a temperature of from 10 to 95° C., and subsequently removing from the product mixture the alcohol introduced and the alcohol liberated in the course of the reaction, by distillation under atmospheric pressure or reduced pressure and at a liquid phase temperature of up to 120° C.

Nonexclusive examples of starting compounds, or combinations thereof, for preparing inventive mixtures include the following:

For component A:
1-aminomethyltrialkoxysilanes, N-aminoethyl-1-aminomethyltrialkoxysilanes, N-aminoethyl-N-aminoethyl-1-aminomethyltrialkoxysilanes, N-methyl-1-aminomethyltrialkoxysilanes, N-n-butyl-1-aminomethyltrialkoxysilanes, N-cyclohexyl-1-aminomethyltrialkoxysilanes, N-phenyl-1-aminomethyltrialkoxysilanes, N-silanes, 1-aminomethylmethyldialkoxysilanes, N-aminoethyl-1-aminomethylmethyldialkoxysilanes, N-aminoethyl-N-aminoethyl-1-aminomethylmethyldialkoxysilanes, N-methyl-1-aminomethylmethyldialkoxysilanes, N-n-butyl-1-aminomethylmethyldialkoxysilanes, N-cyclohexyl-1-aminomethylmethyldialkoxysilanes, N-phenyl-1-aminomethylmethyldialkoxysilanes, 1-glycidyloxymethyltrialkoxysilane, 1-methacryloyloxymethyltrialkoxysilane, N-ureidomethyltrialkoxysilane.

For component B:
methyltrialkoxysilanes, ethytrialkoxysilanes, n-propyltrialkoxysilanes, isobutyltrialkoxysilanes, n-octyltrialkoxysilanes, isobutyltrialkoxysilanes, n-octyltrialkoxysilanes, isooctyltrialkoxysilanes, hexadecyltrialkoxysilanes, phenyltrialkoxysilanes, vinyltrialkoxysilanes.

For component C:
tetraalkoxysilanes, with methoxy, ethoxy, and propoxy being preferred for aforementioned alkoxy groups.

The process of the invention is generally performed as follows:

Usually, first of all, component A, component B where used, and component C where used are introduced into the reaction vessel. A solvent and/or diluent, methanol or ethanol for example, can be added to the alkoxysilane mixture. It is appropriate also to add the amount of water calculated for the reaction, suitably with thorough mixing, with stirring for example. Before or after the addition of water it is possible to heat the reaction mixture and, following the reaction, to work up the resultant product mixture by distillation as stated. The distillative workup of the product mixture is preferably conducted at a temperature in the range from 50 to 120° C. under atmospheric and/or reduced pressure. Here it is possible if desired to add an acid from the group including hydrochloric acid, sulfuric acid, formic add, acetic acid, and citric acid, to name only a few.

In the process of the invention components A, B, and C are used preferably in an A:B:C molar ratio of from 1:0:0 to 1:10:0, preferably from 1:0:0 to 1:4:0, or from 1:0:0 to 1:0:10, preferably from 1:0:0 to 1:0:4, or from 1:0:0 to 1:10:10, preferably from 1:0:0 to 1:4:4.

In the process of the invention it is additionally preferred to use alkoxysilanes having methoxy or ethoxy groups corresponding to the alcohol used as solvent and/or diluent As solvent and/or diluent too it is appropriate to use methanol or ethanol or a mixture of methanol and ethanol. It is also possible, however, to use other alcohols or alcohol mixtures.

In the process of the invention the hydrolysis and condensation of alkoxysilanes used are conducted preferably under atmospheric pressure at a temperature of from 10 to 95° C., more preferably from 60 to 80° C. The reaction is normally conducted under atmospheric pressure. Alternatively the reaction can be conducted under reduced pressure or at superatmospheric pressure. The reaction mixture is appropriately left to react for from 2 to 8 hours before distillative workup of the product mixture is commenced.

Following distillative workup the product of the invention contains preferably less than 5% by weight of the components A, B, and C, and in particular less than 5% by weight, preferably less than 1% by weight, of free alcohols.

Inventive mixtures of catenary, branched, and cyclic siloxanes can be put with advantage to the following exemplary but nonlimiting uses:

The invention accordingly provides for the use of an inventive mixture of catenary, branched, and cyclic siloxanes as a composition for surface modification of pulverulent substances, for silanization of finely divided inorganic fillers and pigments, and for treating mineral, organic, and metallic surfaces, such as concrete, aluminum, steel, and plastics (including PVC and PMMA, to name but two), for example. An inventive mixture of catenary and cyclic siloxane oligomers can be used advantageously for hydrophobicizing surfaces, for instance.

The present invention further provides for the use of an inventive mixture of catenary and cyclic siloxane oligomers as adhesion promoters in filled thermoplastic compounds, e.g., HFFR (Halogen Free Flame Retardants) compounds, for the purpose of obtaining improved mechanical strength and improved electrical insulating properties.

The present invention further provides for use of an inventive mixture of catenary, branched, and cyclic siloxanes as adhesion promoters in adhesives and sealants, including foam sealants, for the purpose of achieving improved service properties, especially controlled cure characteristics, improved mechanical strength, and improved moisture resistance.

The invention further provides for the use of an inventive mixture of catenary, branched, and cyclic siloxanes for modifying and crosslinking organic resins, as binders in inks and paints having improved service properties, and for coating glass fibers, for the purpose of improved adhesion of these glass fibers in plastics reinforced with them, and for the purpose of obtaining improved mechanical strength.

Particularly advantageous properties of the siloxane mixtures of the invention over monomeric organoalkoxysilanes used as standard include the heightened boiling point, the heightened flash point, the lowered vapor pressure, the reduced amount of hydrolysis alcohol released during the application (VOC), and, in particular, the chemical "multifunctional", which allows a particularly targeted application.

What is claimed is:

1. A mixture, comprising:
catenary, branched and/or cyclic siloxanes of the general formula I

$$R_xSiO_{(4-x)/2} \tag{I}$$

wherein
x is 1, 2 or 3,
the substituents R are as follows, with the proviso that at least one group (i) is present,
(i) 1-aminomethyl, N-(2-aminoethyl)-1-aminomethyl, N,N-di(2-aminoethyl)-1-aminomethyl, N—[N'-(2-aminoethyl)-2-aminoethyl)]-1-aminomethyl, N-methyl-1-aminomethyl, N-(n-butyl)-1-aminomethyl, N-cyclohexyl-1-amino-methyl, ureidomethyl or N-phenyl-1-aminomethyl groups,
(ii) hydroxyl, methoxy, ethoxy, 2-methoxyethoxy, isopropoxy, n-propoxy, isobutoxy and/or n-butoxy groups, and
(iii) optionally, alkyl, alkenyl, isoalkyl, cycloalkyl or fluoroalkyl groups having 1 to 18 carbon atoms or aryl groups having 6 to 12 carbon atoms,
with the proviso that not more than one organofunctional group (i) is attached per silicon atom, the quotient of the molar ratio of the moiety (ii) to silicon is from 1 to 2, and the degree of oligomerization for compounds of the general formula I is in the range from 2 to 50.

2. The siloxane mixture as claimed in claim 1, wherein an alkoxy group content of more than 0.001% by weight and less than 60% by weight, based on the weight of the siloxane mixture present.

3. The siloxane mixture as claimed in claim 1, wherein the substituents R (iii) are selected from the group consisting of methyl, ethyl, vinyl, propyl, isobutyl, octyl, hexadecyl, monofluoroalkyl, oligofluoroalkyl, perfluoroalkyl and phenyl groups.

4. The siloxane mixture as claimed in claim 1, having a boiling point >200° C.

5. The mixture of catenary, branched, and cyclic siloxane oligomers as claimed in claim 1, having a flash point >100° C.

6. A process for preparing the siloxane mixture as claimed in claim 1, comprising:
subjecting components A, optionally, B, and, optionally, C, in succession or in a mixture, to targeted hydrolysis and condensation using from 0.5 to 1.8 mol of water per mole of Si and from 0.1 to 10 times the amount by weight of at least one alcohol corresponding to the alkoxy groups of (ii), based on the alkoxysilanes used, at a temperature of from 10 to 95° C., to obtain a product mixture, and
subsequently, removing from the product mixture the alcohol introduced and the alcohol liberated in the course of the reaction, by distillation under atmospheric pressure or reduced pressure and at a liquid phase temperature of up to 120° C.;

wherein component A is at least one 1-organomethyl-functional trialkoxysilane or one 1-organomethyl-functional methyldialkoxysilane, and, component B is at least one alkyl-, alkenyl-, isoalkyl-, cycloalkyl- and/or fluoroalkyl-trialkoxysilane having 1 to 18 carbon atoms and/or phenyltrialkoxysilane and/or alkyl-, alkenyl-, isoalkyl-, cycloalkyl- and/or fluoroalkyl-methyldialkoxysilane having 1 to 18 carbon atoms and/or phenylmethyldialkoxysilane, and component C is a tetraalkoxysilane.

7. The process as claimed in claim 6, wherein components A, B, and C are used in an A:B:C molar ratio of from 1:0:0 to 1:10:0 or from 1:0:0 to 1:0:10 or from 1:0:0 to 1:10:10.

8. The process of claim 6, wherein alkoxysilanes having methoxy or ethoxy groups corresponding to the alcohol are used as solvent and/or diluent.

9. The process of claim 6, wherein the hydrolysis and condensation are conducted under atmospheric pressure at a temperature of from 60 to 80° C.

10. The process of claim 6, wherein the distillative workup of the product mixture is conducted at a temperature in the range from 50 to 120° C. under atmospheric and/or reduced pressure.

11. The process of claim 6, wherein the product obtained following distillative workup contains less than 5% by weight of the components A, B, and C used and less than 5% by weight of free alcohols.

12. An adhesion promoter in adhesives or sealants, a composition for modifying or crosslinking organic resins, a binder in inks or paints, a composition for coating glass fibers, an adhesion promoter in filled thermoplastic compounds, a composition for treating mineral, organic, or metallic surfaces, a composition for rendering surfaces water repellent, a composition for surface modification of pulverulent substances, a composition for silanization of fillers or pigments, or a composition for producing foam sealants, comprising:

the siloxane mixture of claim 1.

13. The siloxane mixture as claimed in claim 2, having a boiling point >200° C.

14. The siloxane mixture as claimed in claim 3, having a boiling point >200° C.

15. The mixture of catenary, branched, and cyclic siloxane oligomers as claimed in claim 2, having a flash point >100° C.

16. The mixture of catenary, branched, and cyclic siloxane oligomers as claimed in claim 3, having a flash point >100° C.

17. The mixture of catenary, branched, and cyclic siloxane oligomers as claimed in claim 4, having a flash point >100° C.

18. The process of claim 7, wherein alkoxysilanes having methoxy or ethoxy groups corresponding to the alcohol are used as solvent and/or diluent.

19. The process of claim 7, wherein the hydrolysis and condensation are conducted under atmospheric pressure at a temperature of from 60 to 80° C.

* * * * *